(12) United States Patent
Delnevo et al.

(10) Patent No.: US 7,422,565 B2
(45) Date of Patent: *Sep. 9, 2008

(54) SUPPORT ELEMENT FOR AN EXTRACORPOREAL FLUID TRANSPORT LINE

(75) Inventors: Annalisa Delnevo, Sant'Agata Bolognese (IT); Luca Caleffi, Mirandola (IT)

(73) Assignee: Gambro Lundia AB, Lund (SE)

( * ) Notice: Subject to any disclaimer, the term of this patent is extended or adjusted under 35 U.S.C. 154(b) by 394 days.

This patent is subject to a terminal disclaimer.

(21) Appl. No.: 10/520,667

(22) PCT Filed: Jun. 12, 2003

(86) PCT No.: PCT/IB03/02239

§ 371 (c)(1),
(2), (4) Date: Jan. 10, 2005

(87) PCT Pub. No.: WO2004/005717

PCT Pub. Date: Jan. 15, 2004

(65) Prior Publication Data

US 2005/0245871 A1    Nov. 3, 2005

(30) Foreign Application Priority Data

Jul. 9, 2002 (IT) .......................... MI2002A1498
Apr. 18, 2003 (IT) .......................... MO2003A0106

(51) Int. Cl.
  *A61M 37/00* (2006.01)
  *A61N 1/30* (2006.01)
  *A61M 1/00* (2006.01)

(52) U.S. Cl. .......................... 604/6.16; 604/27; 604/21; 604/30; 604/80

(58) Field of Classification Search ................. 210/249, 210/321.6, 117, 261, 645; 604/250, 126, 604/4.01, 19, 5.01, 6.09, 6.1, 6.11, 151, 247, 604/262, 645, 258, 29, 6.16

See application file for complete search history.

(56) References Cited

U.S. PATENT DOCUMENTS 4,086,924 A    5/1978    Latham, Jr.

(Continued)

FOREIGN PATENT DOCUMENTS

EP    0 107 440 A1    5/1984

(Continued)

OTHER PUBLICATIONS

Gelman Sciences, "Supor Micro IV Air-Eliminating Filter." Brochure.

(Continued)

*Primary Examiner*—Kevin C. Sirmons
*Assistant Examiner*—Deanna K. Hall
(74) *Attorney, Agent, or Firm*—Finnegan, Henderson, Farabow, Garrett & Dunner, L.L.P.

(57) ABSTRACT

A rigid support element for an infusion line for medical use has a first and second portion rigidly connected to each other and capable of holding a first length of tubing. The first portion incorporates a continuous separator for separating fluid into a gaseous portion and a liquid. This separator has a containing body formed on a support element and a pair of membranes, one hydrophobic and one hydrophilic, interacting with each other.

37 Claims, 12 Drawing Sheets

U.S. PATENT DOCUMENTS

| | | | |
|---|---|---|---|
| 4,187,057 A | | 2/1980 | Xanthopoulos |
| 4,298,358 A | * | 11/1981 | Ruschke .................... 96/174 |
| 4,310,017 A | * | 1/1982 | Raines ..................... 137/533 |
| 4,341,538 A | * | 7/1982 | Vadnay et al. .................. 96/6 |
| 4,515,535 A | | 5/1985 | D'Silva |
| 4,605,503 A | | 8/1986 | Bilstad et al. |
| 4,629,448 A | | 12/1986 | Carlsson et al. |
| 4,705,464 A | | 11/1987 | Arimond |
| 4,824,339 A | | 4/1989 | Bainbridge et al. |
| 4,838,865 A | | 6/1989 | Flank et al. |
| 5,112,298 A | | 5/1992 | Prince et al. |
| 5,147,313 A | | 9/1992 | Dikeman |
| 5,447,417 A | | 9/1995 | Kuhl et al. |
| 5,569,026 A | | 10/1996 | Novak |
| 5,605,540 A | | 2/1997 | Utterberg |
| 5,698,090 A | | 12/1997 | Bene et al. |
| 5,810,770 A | | 9/1998 | Chin et al. |
| 6,071,423 A | | 6/2000 | Brown et al. |
| 6,142,008 A | | 11/2000 | Cole et al. |
| 6,234,992 B1 | | 5/2001 | Haight et al. |
| 6,251,295 B1 | | 6/2001 | Johnson |
| 6,348,156 B1 | | 2/2002 | Vishnoi et al. |
| 6,887,214 B1 | * | 5/2005 | Levin et al. ................ 604/6.11 |
| 6,913,590 B2 | * | 7/2005 | Sorenson et al. ............. 604/29 |
| 2001/0045395 A1 | | 11/2001 | Kitaevich et al. |
| 2005/0245871 A1 | * | 11/2005 | Delnevo et al. ............ 604/126 |

FOREIGN PATENT DOCUMENTS

| | | |
|---|---|---|
| EP | 0 477 973 A1 | 4/1992 |
| EP | 0 601 357 A1 | 6/1994 |
| EP | 0 704 224 A2 | 4/1996 |
| EP | 0 784 988 A1 | 7/1997 |
| EP | 1 066 853 A1 | 1/2001 |
| FR | 2734726 | 12/1996 |
| GB | 2 043 478 A | 10/1980 |
| WO | WO 01/89599 A3 | 11/2001 |

OTHER PUBLICATIONS

"Supor IV-3 Air-Elminating Filter." Brochure.
"Syringe Volume Filters." Brochure.
"Supor Pediatric IV Air-Eliminating Filter." Brochure.
International Search Report for International Application No. PCT/IB03/02239.

* cited by examiner

SUPPORT ELEMENT FOR AN EXTRACORPOREAL FLUID TRANSPORT LINE

CROSS REFERENCE TO RELATED APPLICATION

This application is a national phase application based on PCT/IB2003/002239, filed Jun. 12, 2003, the contents of which are incorporated herein by reference.

BACKGROUND OF THE INVENTION

The present invention relates to a support element for an extracorporeal fluid transport line, and to an extracorporeal fluid transport line, particularly for infusion devices for medical use.

In particular, the support element and the line according to the invention are used in apparatuses for the extracorporeal treatment of blood, for example apparatuses for dialysis and/or plasmapheresis, in order to provide an infusion line which can be connected to an extracorporeal blood circuit associated with the aforementioned apparatuses; the support element and the line in question can also be used for forming an infusion line which can be connected directly to the patient's vascular system.

As is known, a conventional infusion line comprises at least one length of tubing designed to connect a bag containing a specified infusion liquid to an extracorporeal blood circuit or directly to a patient through conventional access means such as needles, catheters or the like. For example, U.S. Pat. No. 5,698,090 in the name of Hospal Industrie describes an infusion line comprising a bag containing a replacement liquid; the infusion line leads to a collection chamber (or bubble trap) in which the infusion liquid can be combined with the blood obtained from a venous branch of an extracorporeal blood circuit.

The collection chamber enables a liquid-air separation process to be conducted, thus preventing the propagation of dangerous gas particles towards the patient. The separated gas can be discharged directly to the exterior, or suitably handled by means of a pneumatic circuit connected to the top of the collection chamber. Downstream of the aforesaid chamber, the blood, having been enriched with the infusion liquid, is returned to the patient's cardiovascular system.

It is clear from the above description that the collection chamber must always contain a specified minimum volume of liquid if it is to function properly; otherwise, if no liquid level were formed in the collection chamber, there would be a risk of transferring gas directly to the patient.

Furthermore, the dimensions of the collection chamber must be such that the blood flow is slowed so that there is time for the gas particles to be separated by moving towards the top of the bubble trap.

In practice, the collection chamber has a radial dimension considerably greater than that of the infusion tube. Consequently, where the manufacture of the line is concerned, the collection chamber must be made in more than one piece and is typically made separately from the rest of the line. The various lengths of tubing forming the infusion line and the various parts of the collection chamber are then assembled by a process which adds to the total cost of the infusion line.

Furthermore, the devices which have been described typically require the presence of level sensors and/or air bubble sensors interacting, by means of a control unit, with at least one safety valve, for example a clamp, which can close the tubing as soon as a critical condition is detected in the bubble trap. Clearly, the fluid collection chamber can separate air from the liquid only when a minimum quantity of liquid is present in the chamber: if the liquid in the collection chamber is used up (this inevitably occurs after a certain time when the infusion liquid has been used up, unless the infusion pump is stopped at the correct time), there will be a transfer of gas towards the patient.

Infusion lines with bubble traps also have some critical aspects in relation to their use: both the tubes and the collection chamber are normally fixed to a face panel, of a blood treatment apparatus for example, or in any case are fixed to a suitable support and positioning system; in particular, the collection chamber must be fixed in a precise way, especially when it interacts with level and/or air bubble sensors. In terms of operation, a significant length of time is therefore required to enable the line to be prepared correctly for use.

Finally, because of their structure, lines with collection chambers are poorly adapted to installation in small spaces.

For the sake of completeness, it should also be mentioned that there is a known air-liquid separator comprising a containing body forming two adjacent chambers separated by a hydrophilic membrane; the containing body has an inlet aperture for a fluid comprising liquid and gas particles. The liquid can pass through the hydrophilic membrane and emerge through an outlet aperture. The gas which reaches the first chamber is discharged through secondary apertures positioned upstream of the hydrophilic membrane, at least one hydrophobic membrane being used at these apertures to prevent the liquid from passing through.

The device which has been described allows the fluid, containing gas particles, to be separated into two parts, namely a liquid phase which emerges from the outlet aperture provided in the second chamber, and a gas phase which is released through the secondary apertures provided in the first chamber. It should be noted that the air separator device which has been described does not require a constant presence of liquid stagnating within it in order to separate the gas; in other words, the fluid passing through the separation device is continuously divided into the liquid, which continues along the line, and the gas, which is discharged to the exterior.

SUMMARY OF THE INVENTION

In this situation, the object of the present invention is to provide a novel support element and a novel infusion line having a very simple, compact and economical structure, and overcoming all the drawbacks described above.

In particular, an object of the present invention is to provide a support element which incorporates the gas separation function in such a way that the corresponding infusion line does not require either the use of a chamber for collecting the fluid upstream of the infusion point, or the presence of any optical or ultrasonic level sensor.

Another object of the invention is to provide a novel support element which facilitates the stage of installing the line in which this element is used, while also minimising the possibility of connection errors.

A further object of the invention is a novel support element which can provide an effective safety function in the line in which it is used without requiring, theoretically, the presence of additional systems for stopping the flow along the line (such as clamps or other devices).

Finally, an object of the present invention is to provide an infusion line which allows a plurality of bags to be incorporated, with a simple means of changing from one bag to the next when the liquid contained in each infusion bag is used up.

These and other objects, which will be made clearer in the following description, are essentially achieved by a support element and an infusion line using this support element according to the descriptions in one or more of the attached claims.

Further characteristics and advantages will be made clearer by the detailed description of a preferred, but not exclusive, embodiment of a support element and an infusion line using this support element according to the present invention.

BRIEF DESCRIPTION OF THE DRAWINGS

This description is provided below with reference to the attached drawings, provided solely for guidance and therefore without restrictive intent, in which.

DETAILED DESCRIPTION

Figure 1:
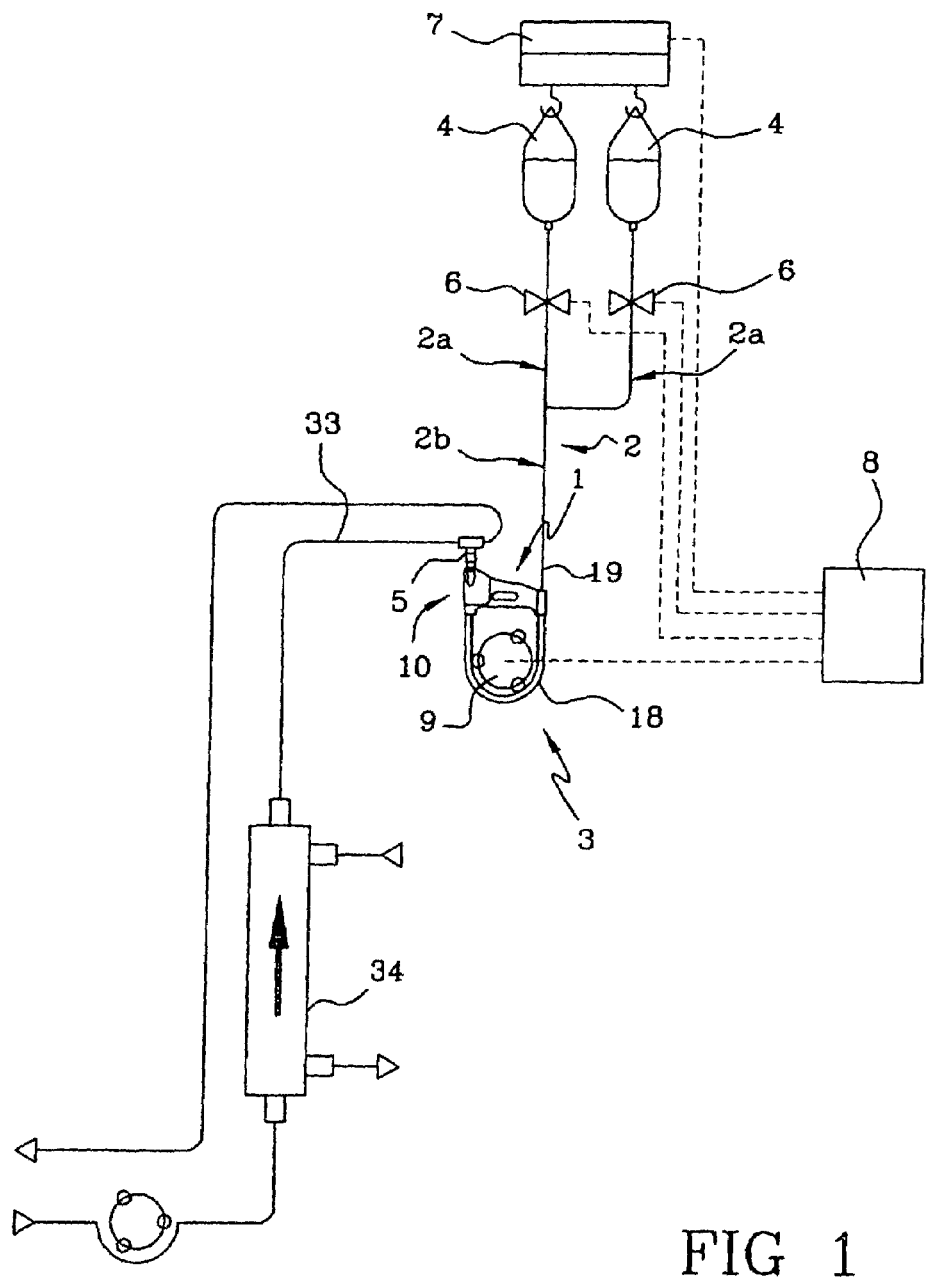
FIG. 1 is a schematic view of an infusion device using the line and the support element according to the invention.
Figure 2:
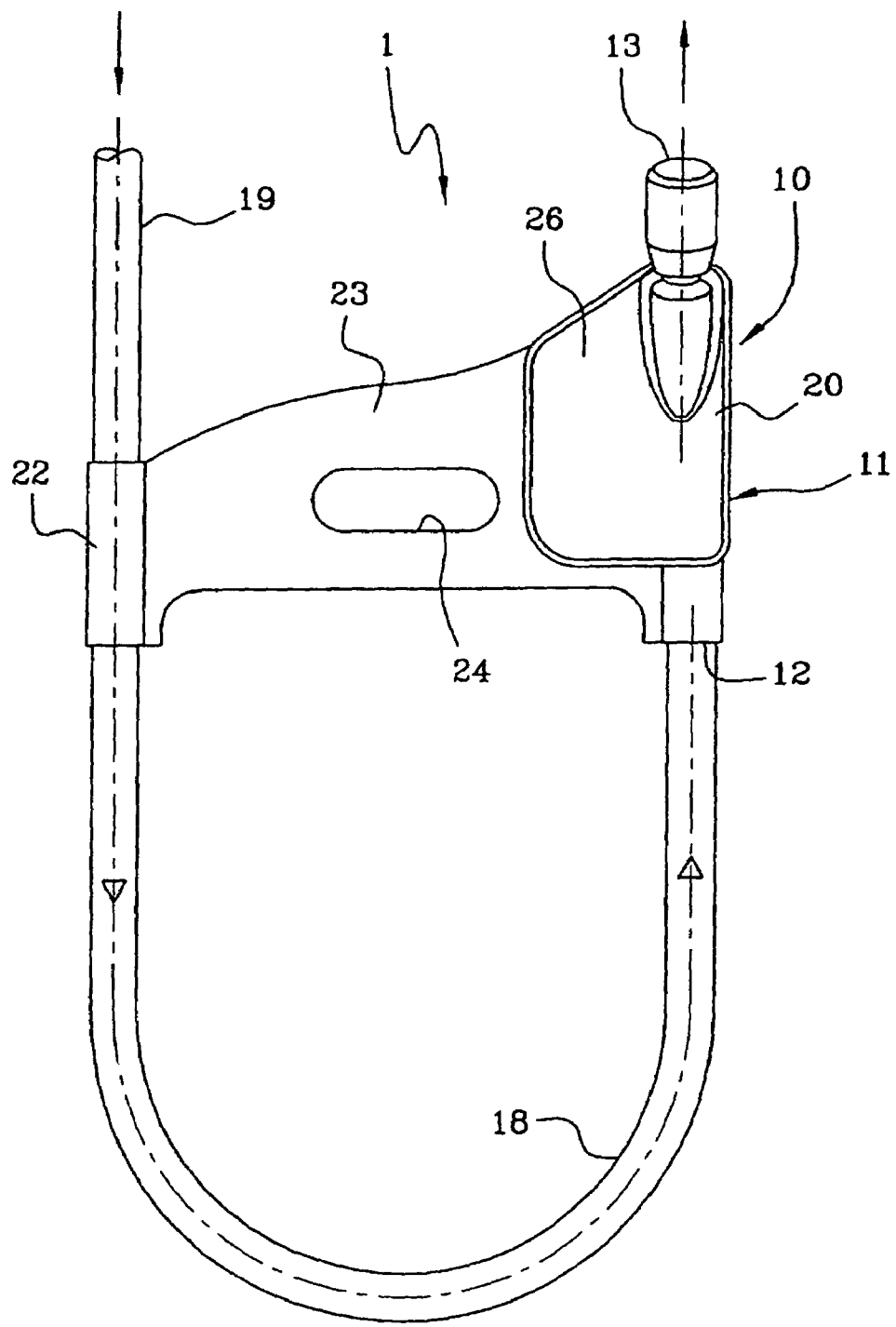
FIG. 2 shows a portion of the device of FIG. 1, comprising a support element according to the invention holding a curved length of tubing.
Figure 3:
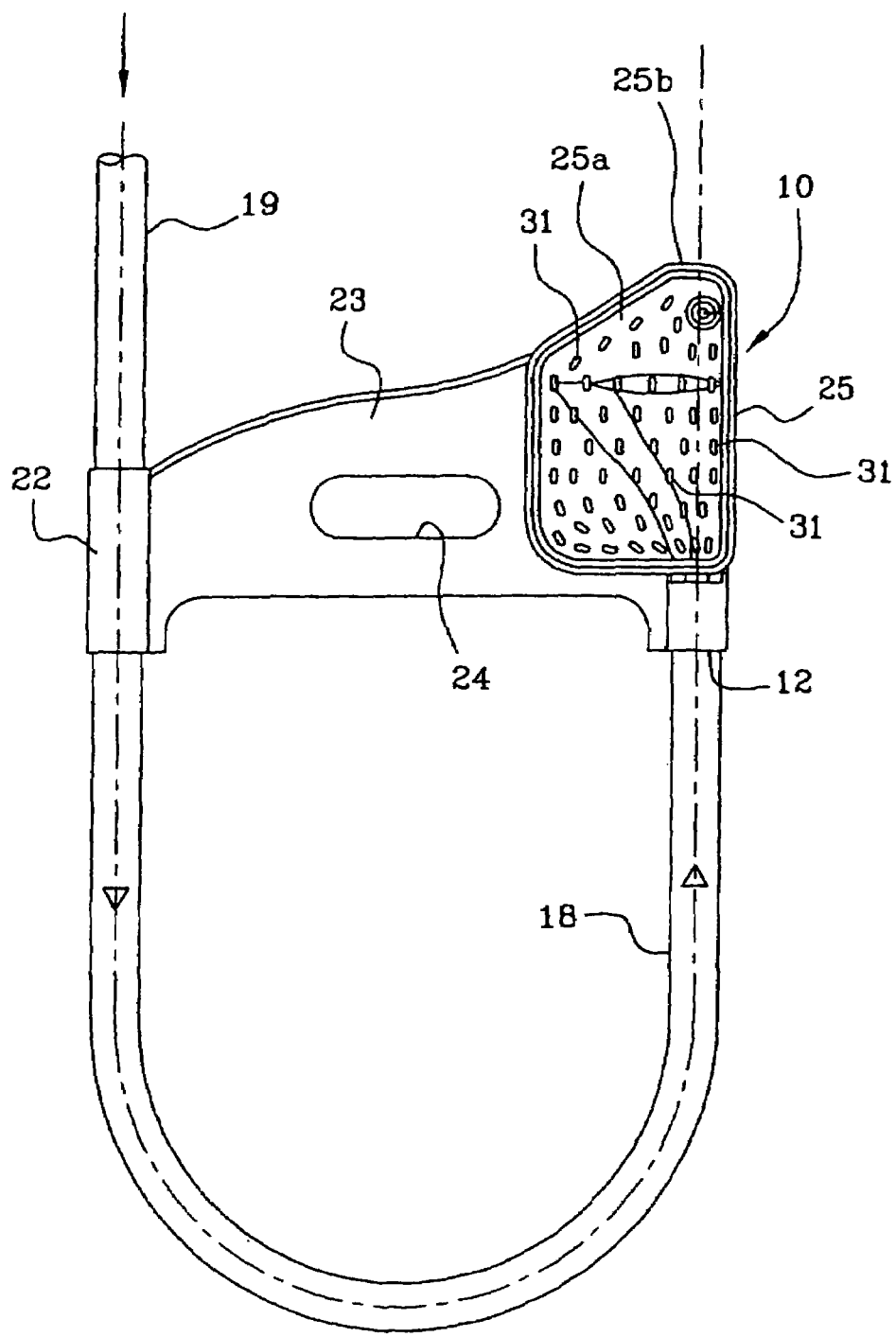
FIG. 3 is a view similar to that of FIG. 2, in which part of the support element has been removed to show the internal structure more clearly.
Figure 6:
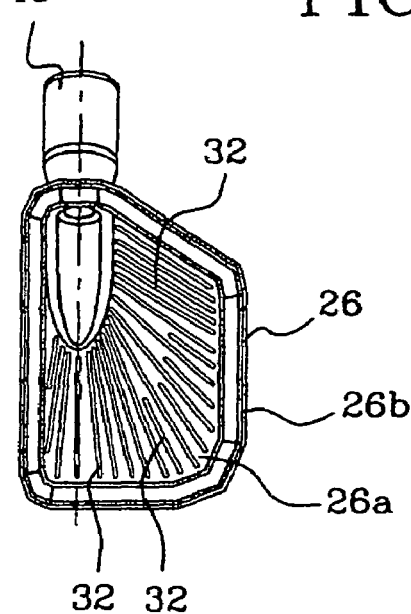
FIG. 6 shows the part of the support element which is removed in the view of FIG. 3.
Figure 4:
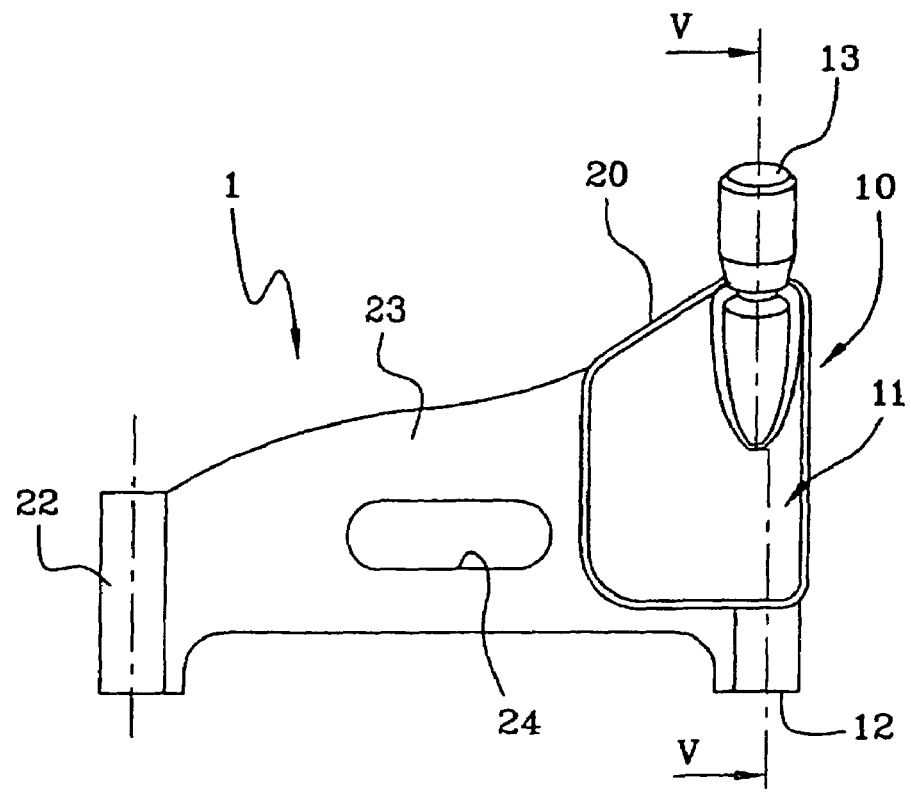
FIG. 4 is a detail view of a support element according to the invention.

With reference to the attached figures, a description will be given of a support element 1 and an infusion line 2 which can be associated with an infusion device 3 for medical use, comprising at least one container 4 designed to hold a specified quantity of a liquid to be infused into a patient; in particular, the infusion point 5 can be positioned in a specified area of an extracorporeal blood circuit, or, alternatively, can be connected directly to the patient.

The infusion device 3 can also comprise a plurality of containers 4, which can be sequentially brought into fluid communication with the infusion point by opening and closing corresponding shut-off elements 6, such as clamps or the like, which may be manually or automatically operated.

A weighing device 7, such as a balance, is associated for operation with the infusion liquid container or containers, to detect the total weight of the container or containers and send a corresponding control signal. In practice, the control signal is a signal related to the total weight measured by the balance 7 during the treatment.

This signal is transmitted to a control unit 8 associated with the weighing device; the control unit 8 can sample and store the weight measured by the balance at finite time intervals, for example at regular intervals. Thus the control unit 8 can determine the actual flow passing through the line and suitably adjust movement means associated with the line whenever a discrepancy is found between the actual flow and the desired flow.

It should be noted that the movement means can comprise at least one pump, for example a peristaltic pump 9, or, for example, in the case of gravity operation, a flow control valve, for example an electromagnetic clamp.

Typically, the desired flow can be set by the user or pre-programmed in the control unit 8 and, in any case, can be a value which is constant or variable with time.

The control unit 8 can determine the decrease in the actual weight of the infusion liquid container, and can adjust the movement means, if necessary, to obtain the desired flow along the line.

Since the total weight of the content of each container 4 is known, the control unit 8 can also detect at least a condition of emptying or end of infusion, and to activate a corresponding control procedure. This procedure can comprise a stage of commanding the movement means (peristaltic pump 9) to stop the transport of fluid along the infusion line 2 and/or a stage of signalling that the container is empty or that a specified volume of liquid has been used up.

If the infusion device 3 comprises two or more liquid containers 4, the infusion line 2 will also have a plurality of branches 2a, each designed to bring a corresponding container into fluid communication with a common part 2b of the line 2 and thus with the infusion point 5. In this case, each branch has a flow shut-off element 6 which can be switched between an open and a closed position, to selectively permit or prevent the passage of fluid.

The flow shut-off elements 6 can be activated manually or commanded sequentially by the control unit 8. For example, the control unit can be programmed so that, when an empty condition of a container is detected, it can command the closing of the shut-off element 6 located in the branch 2a connected to the empty container, and the opening of one of the shut-off elements 6 located in a branch 2a corresponding to a container in which liquid is present. This procedure can be repeated until all the containers have been emptied.

The infusion device in question comprises a continuous fluid separator 10, located in the infusion line 2, for separating the fluid supplied from the container or containers 4 into a gas portion and a liquid portion; this separator can allow only the liquid to continue along the infusion line 2, while separating and discharging towards the exterior any gas bubbles supplied from the container 4.

In particular, when the infusion liquid in a container has been used up, the separator 10 receives any gas and discharges it to the exterior, thus preventing the passage of gaseous substances downstream of the section in which this separator operates.

The continuous separator 10 comprises a containing body 11 having at least one inlet 12 for receiving a fluid supplied from the container, at least a first outlet 13 for receiving a liquid portion of the flow and sending it downstream of the selector to the infusion point, at least a second outlet 14 for receiving the gaseous portion of the fluid and discharging it towards the exterior, and selector means 15 interposed between the inlet 12 and the first outlet 13 and capable of continuously separating the fluid into a gaseous portion and the liquid portion.

The selector means 15 comprises at least one hydrophilic membrane 16 having one side 16a facing the first outlet 13 and one side 16b facing the inlet 12 for receiving the fluid and transferring only liquid towards the first outlet; the selector means 15 also comprises at least one hydrophobic membrane 17 having one side 17a facing the second outlet 14 and one side 17b facing the inlet aperture 12 to receive the fluid and transfer only gas towards the second outlet 14.

With reference to the extension of the infusion line 2, the continuous separator 10 is interposed between the movement means (peristaltic pump 9) and the infusion point 5, and, in particular, is positioned immediately downstream of the movement means.

As can be seen in the attached figures, the device 3 comprises a rigid support element 1, holding opposing portions of a first length of tubing 18 of the line 2 and specifically designed to interact with the movement means (peristaltic pump 9).

In practice, the rigid support 1 holds the first length of tubing 18 in such a way that this first length has a curved shape and a specified axial extension.

The support element 1 is positioned transversely with respect to the mid-line axis of the opposing portions of the first length of tubing 18, and enables the line to be manipulated easily to allow the first length to be easily fitted around a rotor of a peristaltic pump 9.

Upstream of this first length of tubing 18, the infusion line 2 comprises a second length of tubing 19 extending between the container 4 and the rigid support 1 and placed in fluid communication with the first length. As mentioned, the second length of tubing 19 can consist of a single duct connected to a single liquid container 4, or can branch terminally into a plurality of branches 2a, each connected to a corresponding container.

A description will now be given of the detailed structure of the rigid support element 1, which comprises a first lateral portion 20, forming the containing body 11, and a second lateral portion 22, of tubular profile, to which are fixed corresponding ends of the first and the second lengths 18 and 19 of the line 2; the second lateral portion 22 and the first lateral portion 20 are connected rigidly together by a rigid cross-piece 23 provided with at least one through hole 24 which can act as an element for attaching the rigid support to a support wall which is not illustrated; the rigid cross-piece 23 is essentially flat and parallel to a plane in which the first length of tubing 18 lies.

The containing body 11 formed by the first lateral portion 20 comprises a base 25 and a cover portion 26, which interact with each other to form a passage 27 for fluid between the inlet 12, on the one hand, and the first and second outlets 13, 14, on the other hand.

More precisely, the base 25 forms a through channel 28 for putting the passage 27 in fluid communication with the exterior. This through channel 28 extends orthogonally to the plane in which the support element 1 lies, and is located in the proximity of a peripheral area of the base 25; thus, when the infusion device 3 is mounted on the peristaltic pump 9 in operating conditions, the channel 28 is located in a topmost area of the base.

Figure 5:
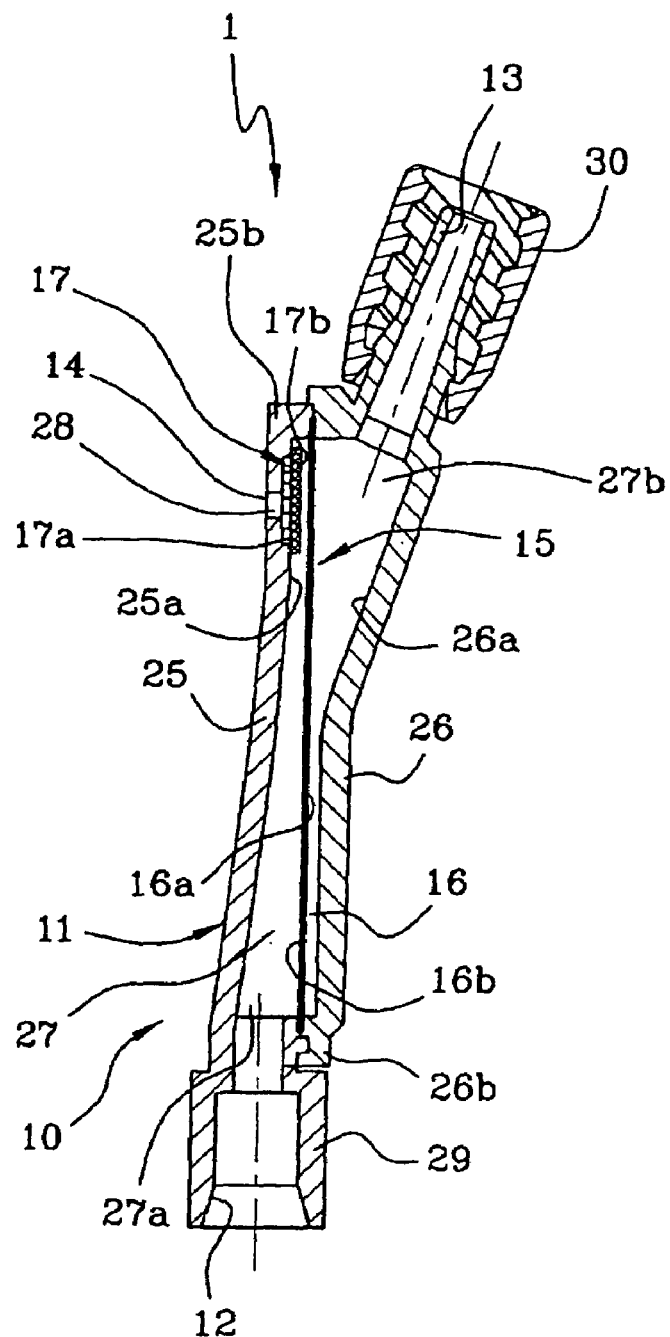
FIG. 5 is a section taken through the line V-V of FIG. 4.
Figure 7:
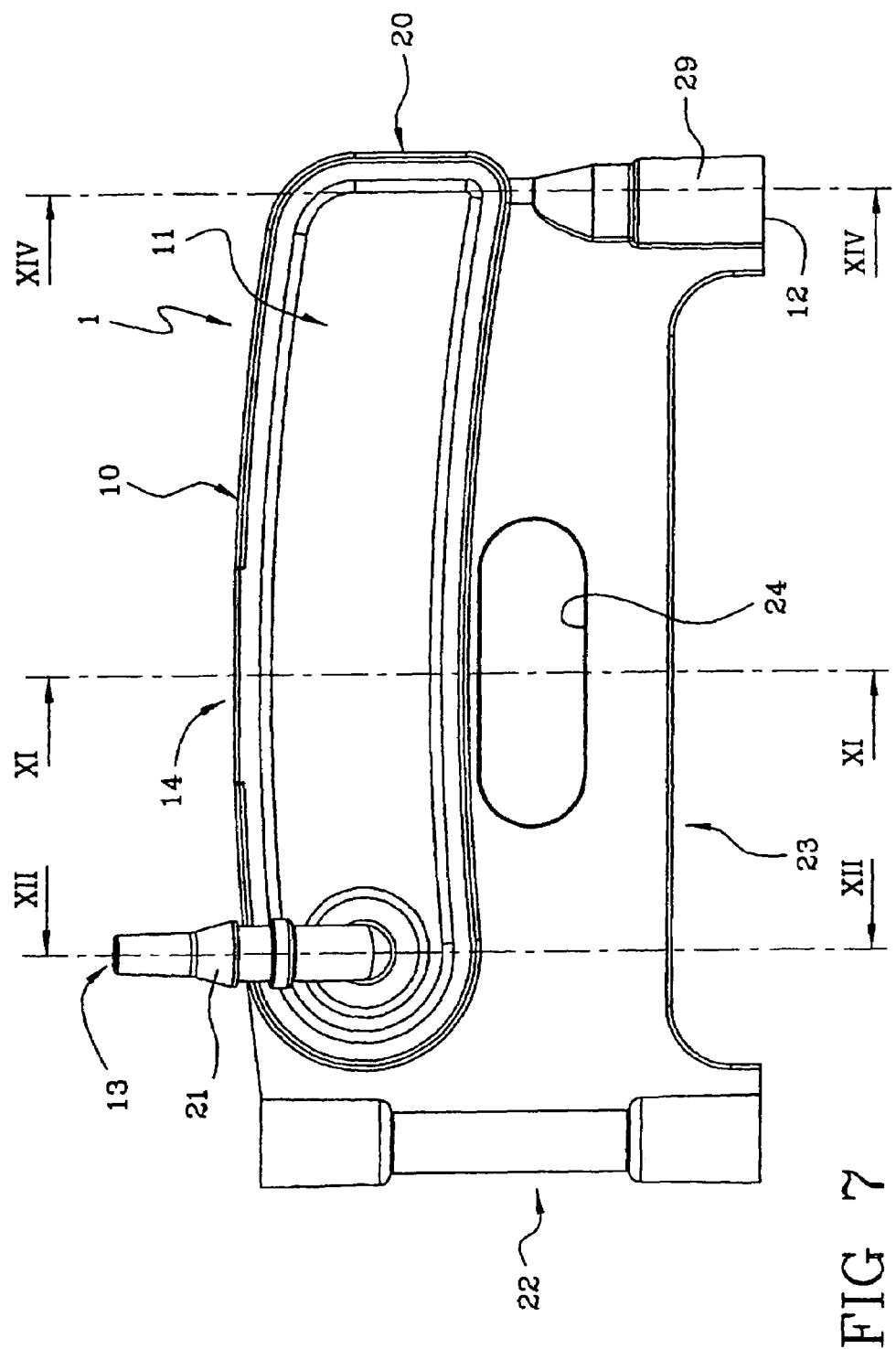
FIG. 7 is a second embodiment of a support element according to the invention, which can be used in substitution for the support element of FIG. 2.
Figure 8:
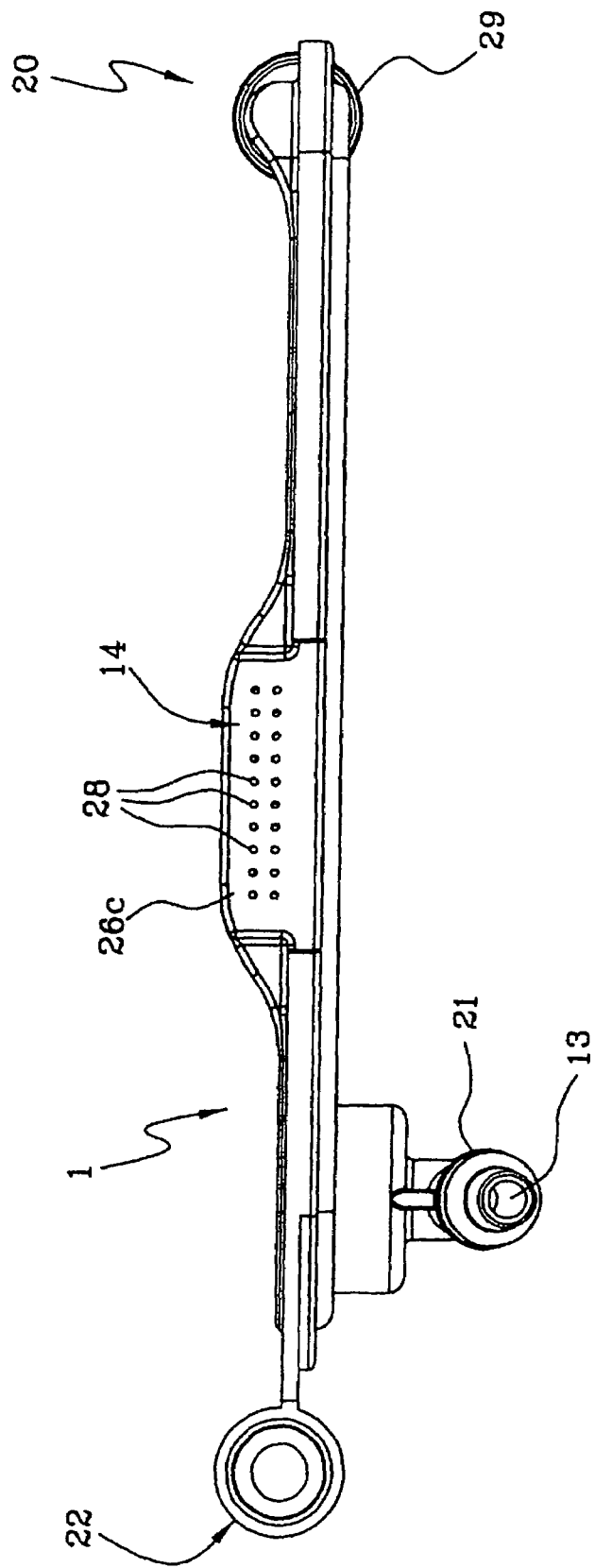
FIG. 8 is a view from above of FIG. 7.

As will be seen in FIG. 5, the passage 27 within the containing body is essentially divided by the hydrophilic membrane 16 into two half-parts or chambers 27a and 27b.

Because of its special positioning, the channel 28 is located in the uppermost point of the chamber 27a (located upstream with respect to the direction of flow) into which the passage is divided, in order to discharge any gas efficiently. For this purpose, the hydrophobic membrane 17 operates in an inlet section of the channel 28 facing the interior of the containing body.

With reference to FIG. 5 again, it will be noted that the base 25 comprises an incorporated first tubular connecting element 29 for receiving one end of the first length of tubing 18. In turn, the cover portion 26 comprises an incorporated second tubular connecting element 30 having an axis of extension inclined with respect to that of the first tubular element 29.

The second connecting element 30 is advantageously of the removable type, for example a Luer connector, and can be connected directly to a mating connector, of the T-shaped type for example, of an extracorporeal blood circuit 33, upstream or downstream of a blood treatment unit 34. Thus, since a direct connection to the extracorporeal blood circuit 33 is possible, it becomes unnecessary to have a tube downstream of the separator 10; this provides the advantage of preventing any possible involuntary blockage which would be difficult to detect by the sensor system associated with the extracorporeal circuit.

It should be noted in this context that any infusion liquid transport tube located downstream of the separator would, if the tube were blocked, cause a pressure stress for certain period, affecting the separator 10 and the membranes 16 and 17 in particular, as well as the liquid seals.

It should also be noted that the rigid support 1 is thin, so that the whole line can occupy very small volumes.

Nevertheless, the efficiency of the system is not reduced by the particular structure of the containing body 11 and the positions of the membranes 16 and 17; in particular, the hydrophilic membrane 16 is interposed between the base 25 and the cover portion 26, and extends essentially through the whole containing body 11; the base 25 and the cover portion 26 comprise corresponding base walls 25a and 26a and corresponding perimeter edges 25b and 26b emerging from the base walls to form the passage through which the fluid is transported.

The hydrophilic membrane 16 extends parallel to the base walls 25a and 26a in a position separated from the walls, thus providing an active surface essentially equal to the area of the containing body 11 seen in plan view.

It should also be noted that the containing body 11 has a plurality of projections 31 and 32 emerging from the base wall 25a of the base and from the base wall 26a of the cover portion. In detail, the projections 31 associated with the base 25 comprise teeth distributed uniformly over the surface of the base wall 25a of the base, while the projections 32 associated with the cover portion 26 comprise angularly spaced deflectors for guiding the liquid flow towards the first outlet 13.

In terms of construction, the base 25 of the containing body, the rigid cross-piece 23 and the second lateral portion 22 are made in a single piece, while the cover portion 26 is fixed to the base 25 after the hydrophobic and hydrophilic membranes 17 and 16 have been placed in position.

Figures from 7 to 14 illustrate a second embodiment of a rigid support element according to the present invention. In the second embodiment, as in the first, the support element is associable to an infusion device 3, such as the infusion device 3 shown in FIG. 1, and engages opposite portions of the first length of tubing 18 of the infusion line 2, as well as a portion of end of the second length of tubing 19.

For reasons of simplicity and greater clarity, in figures from 7 onwards the support element is denoted by 1, like the support element of the first embodiment, illustrated in figures from 1 to 6. Also, in figures from 7 onwards, the elements in the second embodiment which are similar both structurally and functionally to elements of the first embodiment, are denoted by the same numbers as in figures from 1 to 6.

In the second embodiment, the continuous fluid separator 10 incorporates a check valve 36 which is predisposed to prevent back-flow in an opposite direction to the flow direction of the extracorporeal fluid.

The check valve 36, or single-direction valve, is predisposed along the liquid portion line after the liquid has already been separated from the gas portion by the continuous fluid separator 10. The check valve 36 is arranged internally of the separator containing body 11, in a zone comprised between the separator selector means 15 and the first outlet 13 (liquid outlet).

The check valve 36 comprises a mobile obturator organ 37 operating on a liquid passage mouth 35, through which the liquid portion passes. The obturator organ 37 is disc-shaped and is made of an elastomer material (for example silicone). The obturator organ 37 is mobile inside a chamber which, with the obturator in the open position, communicates on one side with the passage mouth 35. In the presence of a flow in the opposite direction to the desired direction, the obturator organ 37 automatically shuts the liquid passage mouth 35, interrupting the back-flow, so that the fluid in the extracorporeal circuit 33 cannot reach the separator 10.

The chamber housing the obturator organ 37 also communicates, with no possibility of shutting-off by the obturator, with the separator first outlet 13, on the opposite side to the liquid passage mouth 35. The check valve 36 is provided with means for preventing the obturator 37 from closing communication with the first outlet 13. The means for preventing are in the present embodiment constituted by at least one projection 38 which emerges from walls delimiting the chamber containing the obturator 37, which projection 38 can interact contactingly with the obturator 37. In the illustrated embodiment a plurality of projections 38 are present, arranged in spoke fashion, each L-shaped and cooperating to contain the obturator 37 laterally.

The liquid passage mouth 35 is associated to the cover portion 26 of the containing body 11. In particular, the passage mouth 35 is arranged on the base wall 26a of the cover portion 26, which the hydrophilic membrane 16 faces at a distanced position therefrom.

As in the first embodiment, the containing body 11 internally affords a fluid passage 27 between the inlet 12 and the first outlet 13. This fluid passage 27 has an upstream portion 27a, comprised between the inlet 12 and the hydrophilic membrane 16, and a downstream portion 27b, comprised between the hydrophilic membrane 16 and the first outlet 13. The base wall 26a, on which the passage mouth 35 is afforded, delimits the downstream portion 27b of the fluid passage.

Figure 14:
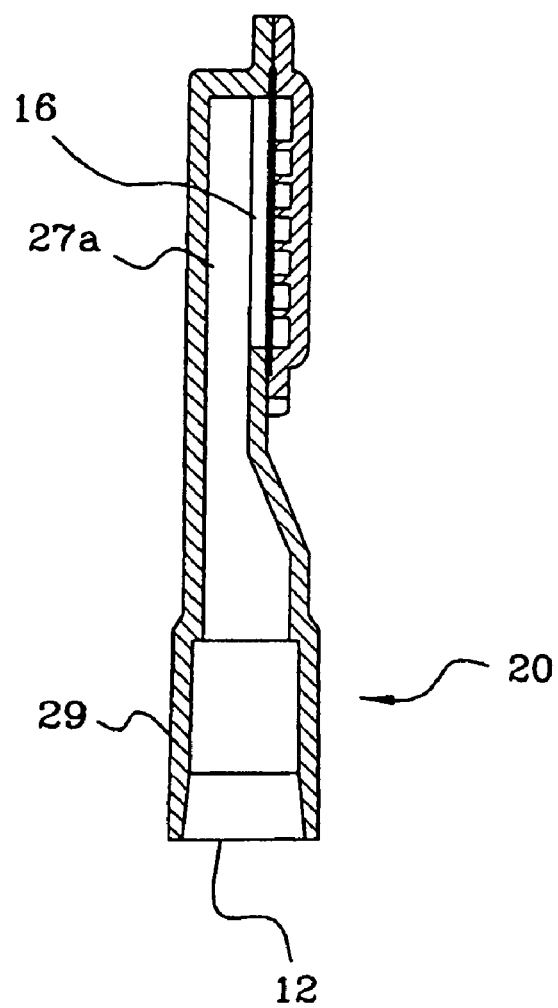
FIG. 14 is a view from inside of a part of the support element which is removed from view in FIG. 9.

The passage mouth 35 is situated in a lateral end zone of the base wall 26a (see FIG. 14), which lateral end zone is opposite to the fluid inlet 12.

Figure 15:
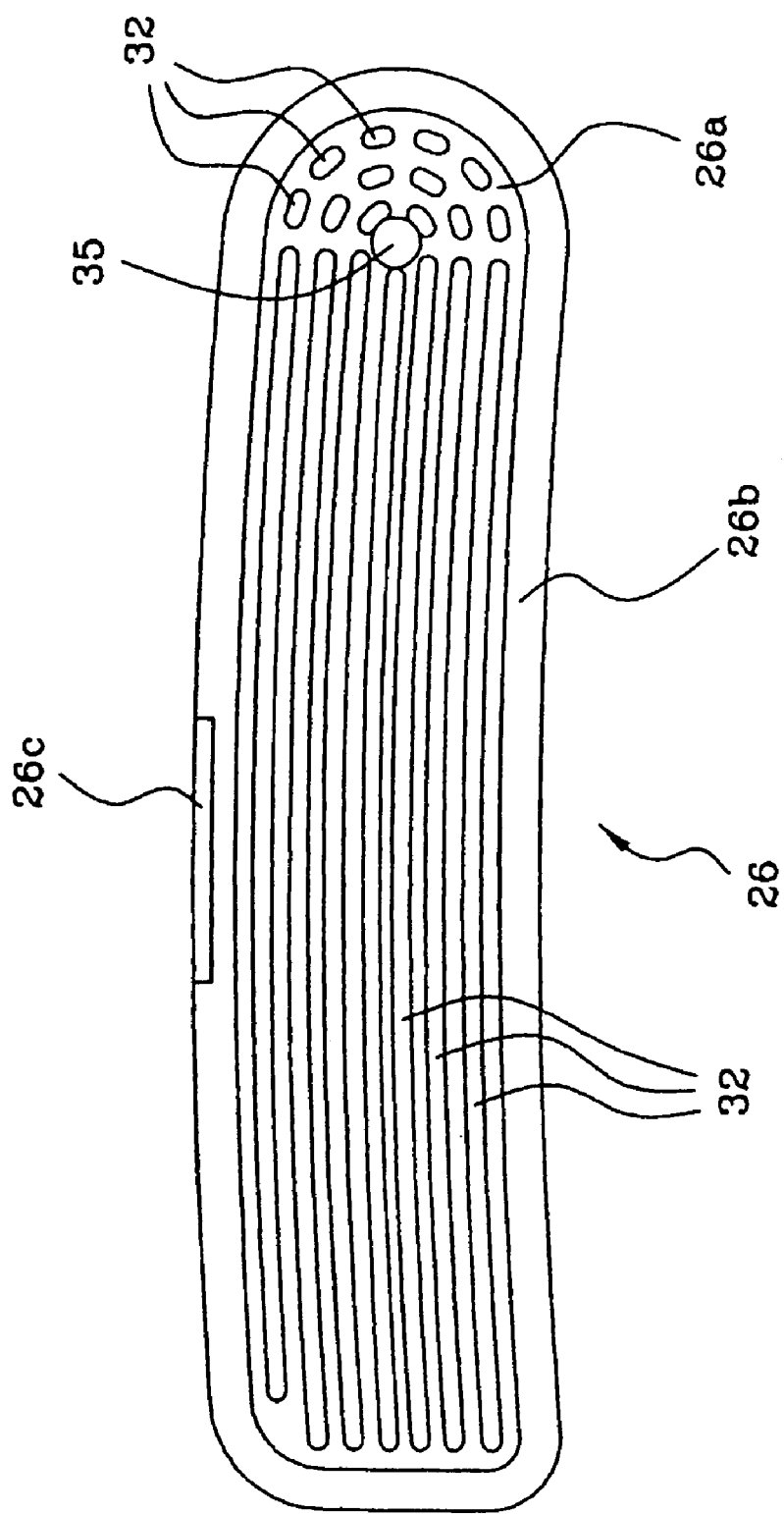
FIG. 15 is a perspective view of a cover portion of a containing body according to an embodiment of the invention.

The projections 32, arranged on the internal side of the base wall 26a, are subdivided into a first group of projections, which reach as far as the passage mouth 35, where the projections 32 are conformed in lines, parallel to one another and extending in a horizontal direction towards the passage mouth 35, defining a plurality of parallel linear conduits oriented in the direction of the liquid portion pathway; and into a second group of projections, arranged beyond the passage mouth 35, in which the projections 32 are like teeth, serrated and shaped as points or small segments, and are oriented tangentially with respect to the centre of the passage mouth 35, as depicted in FIG. 15.

The first outlet 13 is arranged at an upper end of an L-shaped outlet conduit 21. The upper end has an inclined axis with respect to the lie plane of the support element 1. The outlet conduit 21 is solidly associated to the cover portion 26 of the containing body.

The hydrophobic membrane 17, which operates on the second outlet 14 (breather) is situated in an upper zone of the upstream portion 27a of the fluid passage, where the term upper is used in reference to a use configuration in which the lie plane of the first length of tubing 18 is vertical. In the use configuration the hydrophobic membrane 17 is situated at the highest point of the upstream portion 27a, and faces upwards.

In the use configuration, the hydrophobic membrane 17 has a horizontal lie plane, while the hydrophilic membrane 16 has a vertical lie plane.

The hydrophobic membrane 17 is situated above the highest point of the operative filtering surface of the hydrophilic membrane 16. The hydrophilic membrane operative filtering surface does not comprise the perimeter edge of the hydrophilic membrane 16, which is constrained between the perimeter edges of the base 25b and the cover portion perimeter edges 26b.

The upstream portion 27a of the fluid passage has a flat conformation, with one dimension being smaller than the other two, with a lie plane that is parallel to the hydrophilic membrane 16, and thus vertical in the use configuration.

The upstream portion 27a of the fluid passage has a fluid inlet which is arranged in a lower end zone of the upstream portion 27a itself, on an opposite side to the upper second outlet 14 for gas, where the hydrophobic membrane 17 is operative.

The passage section of the upstream portion 27a of the fluid passage increases gradually going from bottom to top, in the direction of the hydrophobic membrane 17, and then towards the second outlet 14. An upper end zone of the upstream portion 27a, superiorly delimited by the hydrophobic membrane 17, is located above the upper edge of the filtering hydrophilic membrane 16.

In the second embodiment, the through channel 28, which places the upstream portion 27a of the fluid passage 27 in communication with the outside atmosphere, through the hydrophobic membrane 17, has a longitudinal axis which extends parallel to the lie plane of the support element 1, and is afforded in a wing 26c of the cover portion 26. The wing 26c projects from an upper end of the cover portion 26, in a transversal direction to the direction of the lie plane of the main body of the cover portion 26. The through channel 28 can be made, as in the illustrated embodiment, in the form of a plurality of uniformly-distributed vertical-axis holes. The hydrophobic membrane 17 is kept in position thanks to a perimeter edge, constrained between an upper mouth of the base 25 and the wing 26c of the cover portion 26.

The base wall 25a of the base, which delimits the upstream portions 27a, has an inclined central part which is arranged at the vertical of the second outlet 14. Thanks to this inclination, the upstream portion 27a of the fluid passage has a central zone, arranged below the vertical of the second outlet 14, having a passage section which progressively increases going from the bottom towards the top thereof. In this central zone, the height of the projections 31 (which cooperate with the projections 32 to prevent excessive deformation of the hydrophilic membrane 16) increases gradually in an upwards direction.

Figure 9:
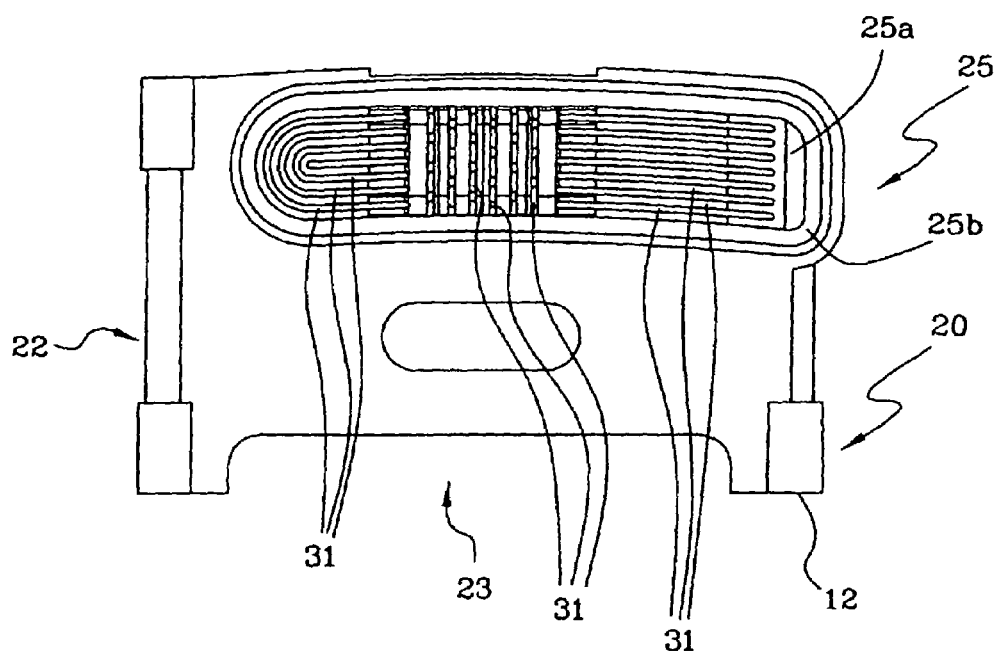
FIG. 9 is the same view as in FIG. 7, with some parts removed better to evidence others.
Figure 10:
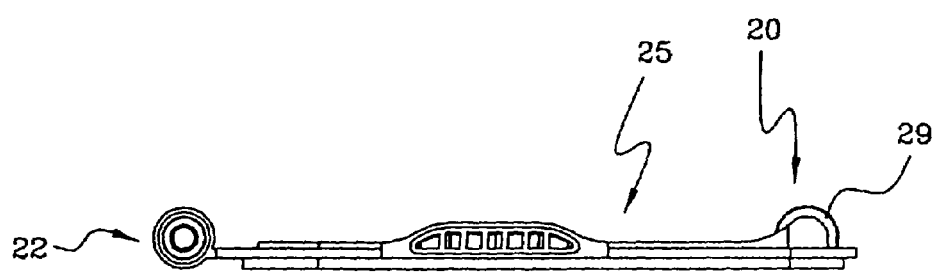
FIG. 10 is a view from above of FIG. 9.
Figure 11:
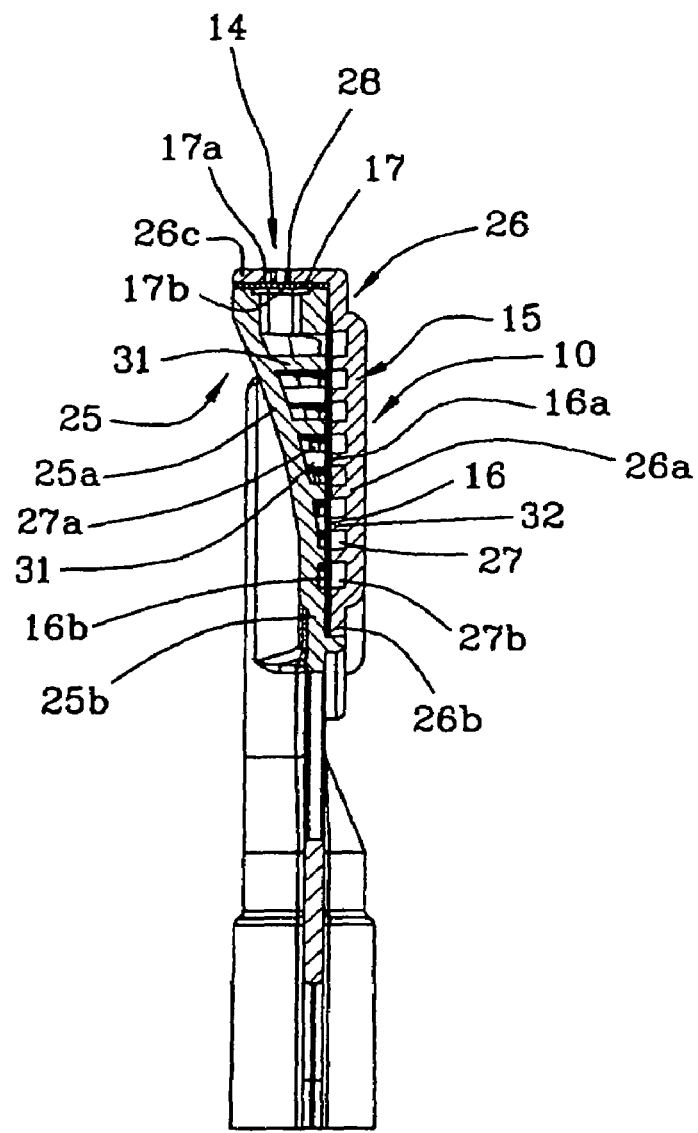
FIG. 11 is a section according to line XI-XI of FIG. 7.
Figure 12:
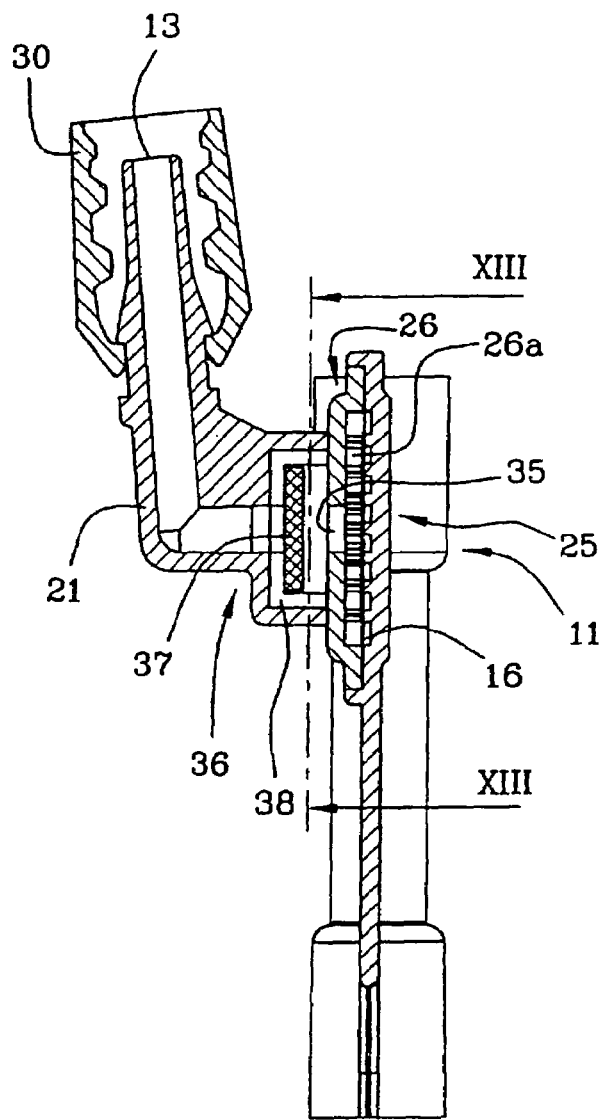
FIG. 12 is a section according to line XII-XII of FIG. 7.
Figure 13:
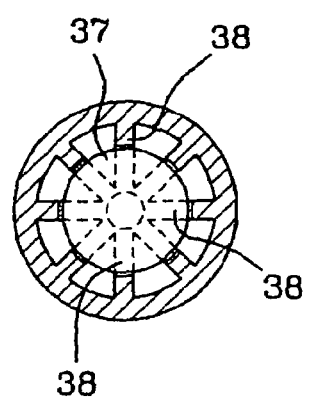
FIG. 13 is a section according to line XIII-XIII of FIG. 12.

In this central zone, the projections 31 are tooth-shaped, and are staggered among themselves with in a horizontal direction. The teeth, for example, can be pointed, aligned in vertical rows, or can be in short segments arranged vertically according to a plan view (FIG. 9); in a lateral end zone, close to the separator fluid inlet 12, the projections 31 are horizontally-arranged lines (on the right in FIG. 9); in another lateral end zone, opposite the fluid inlet, the projections 31 are C-shaped, arranged concentrically one inside another and with the arms of the C-shape elongate in a horizontal direction (on the left in FIG. 9).

The linear projections 31 define linear conduits, which direct the fluid towards the central zone of the upstream portion 27a, lying below the second outlet 14. The C-shaped projections 31 define C-shaped conduits which lead the fluid towards the central zone.

The projections 31 and 32 define two rest planes for both opposite sides 16b and 16a of the hydrophilic membrane, enabling deformations of the membrane in both directions to be limited.

The special arrangement and conformation of the upstream portion 27a, as well as the special arrangement and conformation of the second outlet 14 and the fluid inlet 12, contribute to improving the efficiency of the gas elimination from the fluid, while occupying only a relatively compact space.

In the second embodiment, the containing body 11 is incorporated in the support element 1 and develops prevalently in a transversal direction, from the first lateral portion 20 to the second lateral portion 22. The fluid inlet 12 is situated in the first lateral portion 20, while the first outlet 13, for liquid only, is located in a lateral end zone of the above-mentioned transversal development, beyond the median line of the development and in proximity of the second lateral portion 22. This enables the hydrophilic membrane 16 to have a large active filtration surface, and exploits to the full the space on the rigid cross-piece 23 without increasing the overall mass of the support element 1.

The second outlet 14, for gas, is arranged in an intermediate zone of the transversal development of the containing body 11.

The check valve 36 predisposition prevents back-flow: in particular, the check valve 36 is a guarantee against any risk of passage of blood from the extracorporeal circuit 33 to the infusion line 2. The risk is particularly high in a case where the peristaltic pump 9, for any reason, loses its occluding capacity, i.e. the function of shutting off the first length of tubing 18, by effect of the squeezing of the flexible walls of the tubes in the contact zone between the tubes and the pump rollers. In the absence of this occluding function, blood might flow from the extracorporeal circuit 33, through the infusion line and even up to the containers 4, seriously injuring the patient.

Furthermore, using the check valve 36 prevents inlet of small quantities of blood coming from the extracorporeal circuit 33 into the infusion line 2, in particular the zone thereof comprised between the peristaltic pump 9 and the infusion point 5. This situation might occur due to the operating mode of the peristaltic pump 9, which causes an inconstant pressure in the infusion line 2, with the risk of possible blood leaks during the phase of operation in which the pressure drops.

The continuous fluid separator 10 of air and liquid, which has been described in two possible embodiments, is integrated into a support element 1, predisposed to support a first length of tubing 18, in fluid connection with a second length of tubing 19, also constrained to the support element 1, included in an infusion line 2 which is part of an infusion device 3.

It is possible to use an air-liquid separator, structured like the ones herein described, but not necessarily integrated with the support 1, but independent thereof and included in a fluid transport line, possibly different from the one described above, for deaerating the conveyed fluid.

In a further embodiment, not illustrated, the check valve 36 can be not integrated with the air-liquid separator, but can instead be included in the infusion line, located at a distance after the separator.

LEGEND 1 support element
2 infusion line
2a branches of infusion line
2b common part of infusion line
3 infusion device
4 containers
5 infusion point
6 flow shut-off elements
7 weighing device
8 control unit
9 peristaltic pump
10 continuous fluid separator (or deaerator device)
11 separator containing body
12 separator inlet (fluid inlet)
13 separator first outlet (liquid outlet)
14 separator second outlet (gas outlet)
15 separator selector means
16 hydrophilic membrane (liquid portion passage)
16a hydrophilic membrane side facing liquid outlet
16b hydrophilic membrane side facing fluid inlet
17 hydrophobic membrane (gas portion passage)
17a hydrophobic membrane side facing gas outlet
17b hydrophobic membrane side facing fluid inlet
18 first length of tubing (pump segment)
19 second length of tubing
20 first lateral portion of support element
21 outlet conduit
22 second lateral portion of support element
23 rigid cross-piece of support element
24 through hole of support element
25 base of containing body
25a base wall of base
25b perimeter edge of base
26 cover portion of containing body
26a base wall of cover portion
26b perimeter edge of cover portion
26c upper transversal wing
27 fluid passage within containing body
27a fluid passage half-part upstream hydrophilic membrane
27b fluid passage half-part downstream hydrophilic membrane
28 through channel within containing body
29 first tubular connecting element
30 second tubular connecting element
31 projections associated to containing body base
32 projections associated to containing body cover portion
33 extracorporeal blood circuit
34 blood treatment unit
35 liquid passage mouth
36 check valve
37 mobile obturator organ
38 check valve projections.

What is claimed is:

1. An extracorporeal fluid transport tine comprising:
a support element comprising a first and a second lateral portion and a rigid cross-piece for rigidly connecting the lateral portions; and
a first and a second length of tubing connected to said support element;

wherein the first and second lateral portions hold corresponding portions of the transport line to delimit at least the first length of tubing, said first length of tubing having a curved shape and a specified axial extension, said first length of tubing being configured to interact with movement means;

wherein the first lateral portion incorporates a fluid separator capable of separating fluid into a gaseous portion and a liquid portion, said fluid separator comprising a containing body and at least one hydrophilic membrane;

wherein said containing body has at least one inlet for receiving a fluid and at least a first outlet for receiving a liquid portion of said fluid, said containing body internally defining a fluid passage between said inlet and said first outlet; said containing body comprising a base and a cover portion, interacting with each other to form said fluid passage between said inlet and said first outlet; said base comprising an incorporated first tubular connecting element for receiving a first end of said first length of tubing, said inlet being associated to said first tubular connecting element; said cover portion comprising an incorporated second tubular connecting element, said first outlet being associated to said second tubular connecting element;

wherein said hydrophilic membrane is arranged internally of said fluid passage and interposed between said inlet and said first outlet; said hydrophilic membrane having one side facing said first outlet and one side facing said inlet, for receiving said fluid and transferring only liquid towards said first outlet; said hydrophilic membrane being interposed between said base and said cover portion; and wherein the second lateral portion has a tubular profile and receives a second end of said first length of tubing and one end of said second length of tubing, which are fixed in this portion.

2. The fluid transport line of claim 1, wherein said containing body of said fluid separator comprises at least a second outlet for receiving the gaseous portion of said fluid.

3. The fluid transport line of claim 2, further comprising at least one hydrophobic membrane having one side facing said second outlet and one side facing said inlet, for receiving said fluid and transferring only gas towards said second outlet.

4. The fluid transport line of claim 1, wherein said base forms a through channel for puffing said passage into fluid communication with an exterior, a hydrophobic membrane operating in said channel.

5. The fluid transport line of claim 1, wherein said second tubular connecting element has an axis of extension inclined with respect to that of said first tubular connecting element.

6. The fluid transport line of claim 1, wherein said hydrophilic membrane extends essentially throughout said containing body.

7. The fluid transport line of claim 1, wherein each of said base and said cover portion comprises corresponding base walls and corresponding perimeter edges emerging from said base walls, said hydrophilic membrane extending parallel to said base walls in a position separated from said base walls.

8. The fluid transport line of claim 7, wherein said containing body has a plurality of projections emerging from said base wall of said base.

9. The fluid transport line of claim 7, wherein said containing body has a plurality of projections emerging from said base wall of said cover portion.

10. The fluid transport line of claim 8, wherein said projections emerging from said base wall of said base comprise teeth distributed uniformly over a surface of said base wall of said base.

11. The fluid transport line of claim 9, wherein said projections emerging from said base wall of said cover portion comprise deflectors spaced angularly to guide the flow of liquid towards said first outlet.

12. The fluid transport line of claim 1, wherein said base of said containing body, said rigid cross-piece and said second lateral portion are made in a single piece.

13. The fluid transport line of claim 1, wherein said rigid cross-piece is essentially flat and parallel to a plane in which said first length of tubing lies.

14. The fluid transport line of claim 1, wherein said fluid separator incorporates at least one check valve predisposed to prevent a flow in said transport line which is inverse to a desired transport direction.

15. The fluid transport line of claim 14, wherein said check valve is predisposed along a pathway of said liquid portion, after said liquid portion has been separated from said gaseous portion by said fluid separator.

16. The fluid transport line of claim 15, wherein said check valve is arranged internally of said containing body in a zone comprised between said hydrophilic membrane and said first outlet.

17. The fluid transport line of claim 14, wherein said check valve comprises a mobile obturator organ, which operates on a passage mouth of said liquid portion.

18. The fluid transport line of claim 17, wherein said passage mouth is associated with said cover portion of said containing body.

19. The fluid transport line of claim 18, wherein said hydrophilic membrane is facing and distanced from a base wall of said cover portion, said passage mouth being associated with said base wall.

20. The fluid transport line of claim 2, wherein said hydrophobic membrane is situated in an upper zone of a fluid passage portion located upstream of said hydrophilic membrane, said hydrophobic membrane facing upwards, with reference to a use configuration of said support element, in which configuration said first length of tubing has a vertical lie plane.

21. The fluid transport line of claim 20, wherein said upstream passage portion for passage of fluid has at least one passage section which increases in a direction towards said hydrophobic membrane.

22. The fluid transport line of claim 20, wherein said hydrophobic membrane is located superiorly with respect to an upper point of the operative surface of said hydrophilic membrane.

23. The fluid transport line of claim 1, wherein said containing body has a development which is prevalently in a transversal direction proceeding from said first lateral portion to said second lateral portion, said first outlet being located in a lateral end zone of said transversal development, in proximity of said second lateral portion.

24. The fluid transport line of claim 23, wherein said second outlet is arranged in an intermediate zone of said transversal development.

25. The fluid transport line of claim 1, wherein said hydrophilic membrane has a vertical lie plane, with reference to a use configuration in which said first length of tubing has a vertical lie plane.

26. A gas-liquid separator, comprising:
a containing body having at least one inlet for receiving a fluid and at least a first outlet for receiving a liquid portion of said fluid, and at least a second outlet for receiving a gaseous portions of said fluid, said containing body comprising a base and a cover portion, interacting with each other to form a fluid passage between said inlet and said first and second outlets, the first outlet being arranged at an end of an outlet conduit solidly associated to said cover portion; said cover portion comprising an incorporated tubular connecting element of the removable type, said tubular connecting element being coupled to said outlet conduit;

at least one filtering element arranged internally of said fluid passage and having a side which faces said first outlet, and a side which faces said at least one inlet, for receiving said fluid and transferring only liquid towards said first outlet, said filtering element dividing said fluid passage into an upstream portion thereof, situated between said at least one inlet and said filtering element, and a downstream portion thereof, situated between said filtering element and said first outlet, said second outlet being operatively associated with said upstream portion of said fluid passage, said filtering element being hydrophilic and being interposed between said base and said cover portion;

a hydrophobic element operating on said second outlet;

at least one check valve predisposed along a pathway of said liquid portion, after said liquid portion has been separated from said gaseous portion by said filtering element; said check valve being arranged internally of said containing body in said downstream portion of said fluid passage; said check valve comprising a mobile obturator organ, which operates on a passage mouth of said downstream portion; said passage mouth being associated with said cover portion of said containing body; said obturator organ being mobile inside a chamber which, with the obturator organ in an open position, communicates on one side with said passage mouth and, on the opposite side to the passage mouth, with said first outlet.

27. The separator of claim 26, wherein said second outlet is situated in an upper zone of said upstream portion of said fluid passage, with reference to a use configuration of said separator.

28. The separator of claim 27, wherein at least a part of said upstream portion of said fluid passage has a passage section which increases gradually in an upwards direction, with reference to a use configuration of said separator.

29. The separator of claim 27, wherein said hydrophilic element is flat, with a lie plane arranged vertically, with reference to a use configuration of said separator.

30. The separator of claim 26, further comprising a hydrophobic element operating on said second outlet, said filtering element and said hydrophobic element being flat and having lie planes arranged one transversally with respect to another.

31. The separator of claim 27, wherein said at least one fluid inlet is arranged in a lower zone of said upstream portion of said fluid passage, with reference to a use configuration of said separator.

32. The separator of claim 26, wherein said containing body comprises at least two base walls, which delimit said fluid passage and which face opposite sides of said filtering element, said filtering element being distanced from said base walls, a plurality of projections emerging from said base walls defining two rest planes for said opposite sides of said filtering element.

33. The fluid transport line of claim 1, comprising a container of a liquid to be infused into a patient, said second length of tubing extending between said container and said support element.

34. The separator of claim 26, wherein said filtering element is facing and distanced from a base wall of said cover portion, said passage mouth being associated with said base wall.

35. The separator of claim 26, wherein said tubular connecting element of the removable type comprises a luer connector.

36. The separator of claim 26, wherein said passage mouth is arranged on a base wall of said cover portion and faces said filtering element at a distanced position therefrom.

37. The separator of claim 36, wherein a plurality of projections is arranged on an internal side of said base wall.

* * * * *

UNITED STATES PATENT AND TRADEMARK OFFICE
CERTIFICATE OF CORRECTION

PATENT NO. : 7,422,565 B2 Page 1 of 1
APPLICATION NO. : 10/520667
DATED : September 9, 2008
INVENTOR(S) : Annalisa Delnevo et al.

It is certified that error appears in the above-identified patent and that said Letters Patent is hereby corrected as shown below:

In claim 1, column 10, line 62, "tine" should read --line--.

In claim 4, column 11, line 47, "puffing" should read --putting--.

In claim 26, column 13, line 2, "portions" should read --portion--.

Signed and Sealed this

Twenty-eighth Day of October, 2008

JON W. DUDAS
*Director of the United States Patent and Trademark Office*